United States Patent
Kupferschmid et al.

(10) Patent No.: US 6,818,005 B2
(45) Date of Patent: Nov. 16, 2004

(54) SURGICAL, TUBULAR-SHAFTED INSTRUMENT

(75) Inventors: Bernhard Kupferschmid, Emmingen-Liptingen (DE); Pedro Morales, Tuttlingen (DE); Dieter Weisshaupt, Immendingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 403 days.

(21) Appl. No.: 10/055,795

(22) Filed: Jan. 22, 2002

(65) Prior Publication Data

US 2002/0095177 A1 Jul. 18, 2002

Related U.S. Application Data

(63) Continuation of application No. PCT/EP00/06125, filed on Jun. 30, 2000.

(30) Foreign Application Priority Data

Jul. 26, 1999 (DE) .......................................... 199 35 042

(51) Int. Cl.$^7$ ................................................. A61B 17/32
(52) U.S. Cl. ........................ 606/170; 606/205; 279/30
(58) Field of Search ............................... 606/174, 205, 606/170, 180; 279/2.23, 75, 76, 30

(56) References Cited

U.S. PATENT DOCUMENTS 3,975,032 A * 8/1976 Bent et al. ..................... 279/30
4,199,160 A * 4/1980 Bent ............................. 279/30
5,505,737 A * 4/1996 Gosselin et al. ............... 606/79
5,569,256 A   10/1996 Vaughn et al.
5,741,263 A    4/1998 Umber et al.

FOREIGN PATENT DOCUMENTS

DE   41 03 663    8/1992
DE   298 03 734   4/1998

* cited by examiner

Primary Examiner—Julian W. Woo
(74) Attorney, Agent, or Firm—Barry R. Lipsitz

(57) ABSTRACT

A surgical, tubular-shafted instrument comprises a shaft, an operating rod mounted for displacement in the shaft, a handle part for actuating the operating rod and a connector that detachably connects the handle part to the shaft. The shaft is secured in an axial direction in an inner sleeve of the handle by a locking member that is displaceable radially in the inner sleeve and dips into a recess of the shaft. The radial outward movement of the locking member is limited by a stop element that is displaced into a position releasing the radial outward movement of the locking member. A holding element fixes the stop element in a release position and can be acted upon by the shaft to release the stop element due to displacement of the shaft in the inner sleeve. The holding element is guided for displacement in the handle part outside the inner sleeve.

34 Claims, 4 Drawing Sheets

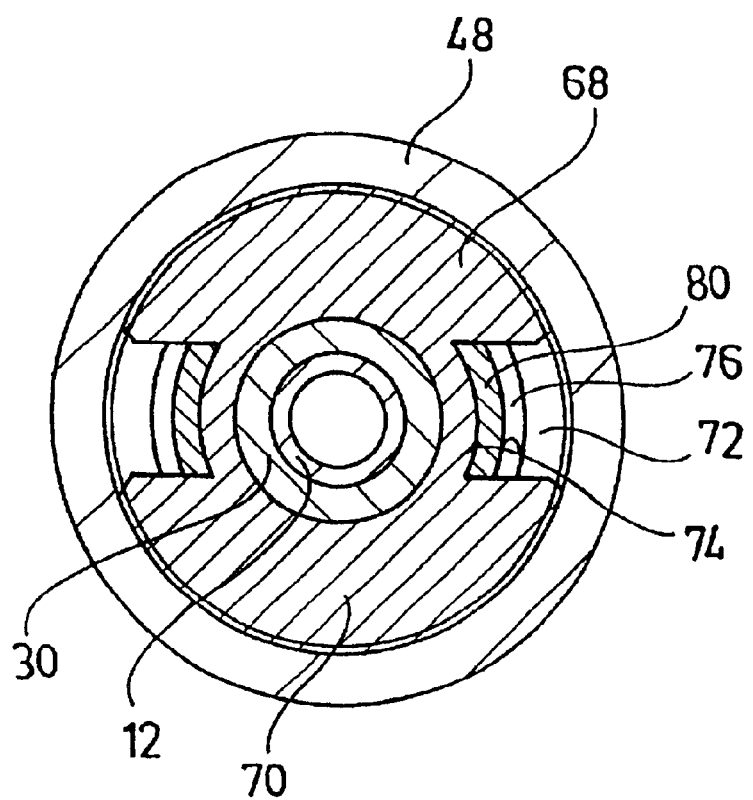

SURGICAL, TUBULAR-SHAFTED INSTRUMENT

The present is in Continuation of International Application No. PCT/EP00/06125 of Jun. 30, 2000, which is incorporated herein by reference in its entirety and for all purposes.

BACKGROUND OF THE INVENTION

The invention relates to a surgical, tubular-shafted instrument comprising a shaft, an operating rod mounted for displacement in the shaft, a handle part for actuating the operating rod and connecting means which connect the handle part and the shaft detachably to one another, wherein the shaft can be secured in an axial direction in an inner sleeve of the handle part by means of a locking member which is displaceable radially in the inner sleeve and dips into a recess of the shaft, the radial outward movement of the locking member being limited by a stop element which can be displaced into a position releasing the radial outward movement of the locking member, and wherein holding means are provided, by means of which the stop element can be fixed in a release position and which can be acted upon by the shaft in such a manner that this fixing can be released due to displacement of the shaft in the inner sleeve.

Such a tubular-shafted instrument is described, for example, in German patent application 198 09 120.6 which is not a prior publication.

In the case of this known tubular-shafted instrument, corresponding connecting means are also provided which connect the operating rod detachably to the handle part.

The object of the invention is to simplify the construction of such an instrument, in particular, with a view to reducing the necessary space required for the connecting means.

SUMMARY OF THE INVENTION

This object is accomplished in accordance with the invention, in a tubular-shafted instrument of the type described at the outset, in that the holding means comprise a holding element which is guided for displacement in the handle part outside the inner sleeve.

In the handle part, a corresponding space must be provided outside the inner sleeve in order to arrange the connecting means. In the case of the tubular-shafted instrument described in DE 198 09 120.6, the holding element is guided for displacement within the inner sleeve. This makes it necessary for the inner sleeve to have an interior space which has a greater diameter than the shaft. As a result of the inventive arrangement of the holding element, a space which is, in any case, already present is better utilized and, as a result, the inner sleeve may have smaller dimensions and, therefore, the handle part can be designed, altogether, to be more compact and, in particular, have smaller dimensions.

Furthermore, it is provided in the case of DE 198 09 120.6 for the same locking members to lock the shaft to the handle part in the connection position and fix the release position by means of the holding element. The reason for this is, since not only the shaft but also the holding element is guided within the inner sleeve, that only one radial inwards movement of a locking member can also bring about locking. In the case of the inventive tubular-shafted instrument, the locking of the shaft and the locking of the release position may, on the other hand, be decoupled via the holding element. As a result, space-saving locking mechanisms may be achieved which simplify the construction of an inventive tubular-shafted instrument.

It is particularly advantageous when the holding element is guided for displacement about the inner sleeve. The inner sleeve is then located within the holding element. A displacement of the holding element against the stop element may be brought about in a simple manner in order to thus take care of any fixing of the release position.

It is particularly favorable when the holding element has a coupling element for the shaft which points into the interior of the inner sleeve. In this way, the holding element located outside the inner sleeve can be displaced via the shaft or the holding element can act on the shaft. So that the coupling element can act on the shaft at all, the inner sleeve must have a recess for the coupling element.

It is particularly favorable when the shaft has a guiding recess for the coupling element. The holding element can be guided by means of this guiding recess via the shaft with concerted intermediary of the coupling element, and, on the other hand, the coupling element can guide or secure the shaft accordingly.

It is particularly favorable when the holding element exerts an advancing force on the shaft in a distal direction when the release position of the locking member, which is radially displaceable in the inner sleeve, is reached. The coupling element can then act on the shaft via the recesses. The holding element therefore functions as an ejector for the shaft.

It is particularly advantageous when the shaft can be secured by the coupling element so as to be non-rotatable with respect to the inner sleeve. As a result, it is possible to secure the shaft in the handle part in the connection position in addition to the locking with the locking members. An inventive tubular-shafted instrument can then absorb greater forces and, in particular, greater torques without the shaft becoming detached. However, the locking position may also be achieved more easily since an engagement of the coupling element allows only a linear displacement of the shaft. With a corresponding adjusted alignment between the locking member and the coupling element, it is ensured that the locking member can dip into the recess on the shaft in the connection position.

Favorably, the holding element is guided for displacement surrounding the stop element. As a result, a displacement guidance for the holding element is provided, on the one hand, and, on the other hand, the spatial requirements for this displacement guidance are minimized.

Favorably, a spring for the relative displacement between holding element and stop element is seated between holding element and stop element and is tensioned in the connection position of the shaft. As a result, an automatic displacement of the holding element may be brought about upon the release of the connection position and thus this holding element can be transferred automatically into a position, in which the release position is fixed. As a result, the holding element may also be used advantageously as an ejector for the shaft upon release of the connection position.

It is particularly advantageous when the spring force acts contrary to the direction, in which the stop element can be displaced for the release of the radial outward movement of the locking member. As a result, an automatic fixing of the release position may be brought about in a constructionally simple manner upon the release of the locking position.

In order, in particular, to bring about a simple and secure return of the holding element during the transition from the release position into the locking position, it is advantageous when the spring seated between holding element and stop element is designed and tensioned such that it exerts a smaller spring force in the connection position than a return spring which is seated between stop element and inner sleeve and serves to displace the stop element out of a release position into the connection position when the fixing of the holding element is released. As a result, the first named spring can be tensioned again during the return movement in order to displace the holding element upon release of the connection position.

In a particularly simple embodiment from a constructional point of view, the holding means comprise a locking member which is displaceable radially in the stop element and dips into a recess of the inner sleeve in the release position of the stop element. As a result, the stop element may be secured on the inner sleeve in a simple manner in order to fix the release position for the shaft in this way.

Favorably, the radial outward movement of the locking member is limited in the release position of the stop element by the holding element as stop. An essential function of the holding element is to block the locking member for the fixing of the release position.

Favorably, the holding element has a guiding recess for the locking member, in which this is guided for longitudinal displacement during the displacement of the holding element from its position in the connection position into a position in the release position of the stop element. This guiding recess allows the transition between a defined connection position and a defined release position, wherein the latter can then be fixed.

Favorably, the stop element is designed as a sleeve surrounding the inner sleeve in order to bring about a secure displacement guidance and minimize the spatial requirements.

Furthermore, it is advantageous when the holding element is designed as a sleeve surrounding the stop element in order to likewise bring about a secure displacement guidance and minimize the spatial requirements.

Advantageously, a guide means for the holding element is formed in the handle part in an annular space limited by the stop element. As a result, the spatial requirements can, again, be minimized and a displacement guidance formed in a simple manner.

The further object underlying the invention is to improve a tubular-shafted instrument such that a connection position can be achieved in a simple manner.

This object is accomplished in accordance with the invention, in a tubular-shafted instrument of the type described at the outset, in that the holding means have a holding element with a coupling element, by means of which the shaft can be non-rotatably secured with respect to the inner sleeve due to engagement in a corresponding counterelement of the shaft.

In this way, in addition to the locking member which locks the shaft to the inner sleeve, an additional coupling element independent thereof is provided which secures the shaft non-rotatably. The holding element is already present, in any case, in order to fix the release position. The additional securing against rotation is therefore brought about with the inventive solution by means of minimal constructional resources.

Favorably, the holding element is, for this purpose, guided for displacement outside the inner sleeve in order to keep the spatial requirements to a minimum in this way.

Furthermore, it is advantageous when the counterelement is formed by a recess in the shaft. Such a recess may be produced in a simple manner. As a result of limiting walls of the recess, stop surfaces can be made available which bring about the securing against rotation and, on the other hand, a displacement of the holding element for fixing the release position may also be achieved via such stop surfaces when inserting the shaft into the inner sleeve over the coupling elements.

Additional variations of embodiments of the invention as well as their advantages have already been described above. Reference is made to this description.

The following description of preferred embodiments of the invention serves to explain the invention in greater detail in conjunction with the drawings.

BRIEF DESCRIPTION OF THE DRAWINGS

FIG. 3 shows a view similar to FIG. 2 with a released shaft (release position) and FIG. 4 shows a sectional illustration along the line 4—4 in FIG. 2.

DETAILED DESCRIPTION OF THE DRAWINGS

Figure 1:
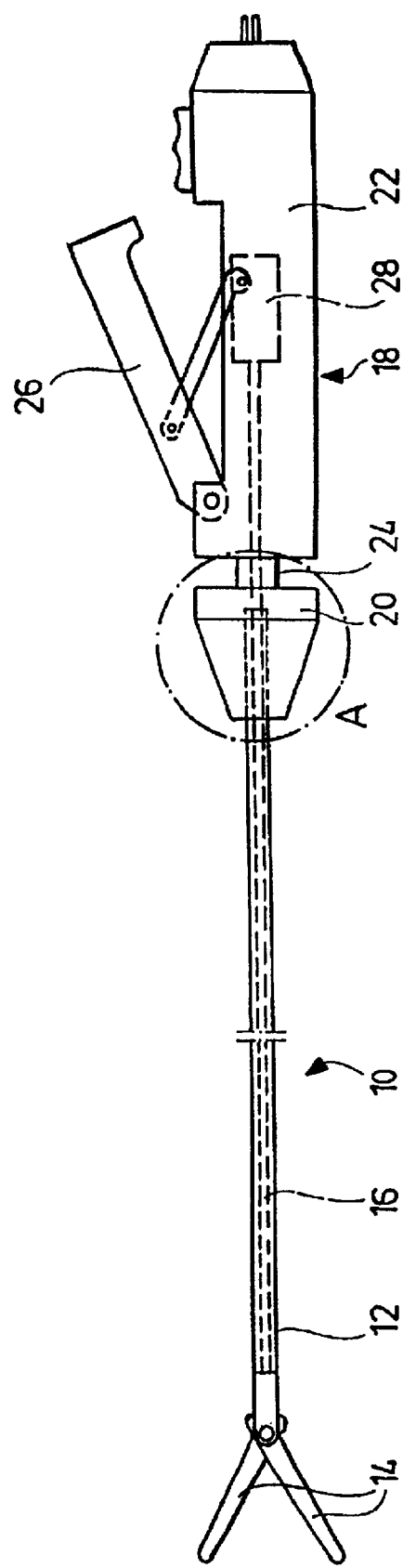
FIG. 1 shows a side view of a tubular-shafted instrument with a handle part arranged coaxially to the tubular shaft.

The tubular-shafted instrument illustrated in FIG. 1 and designated as a whole as 10 comprises a tubular shaft 12, at the distal end of which two movable tools 14 are mounted, for example, forceps jaws or cutting edges of a cutting tool. In the interior of the shaft 12 an operating rod 16 is mounted for longitudinal displacement coaxially to it and, in particular, a push and pull rod which pivots the tools 14 in opposite directions via a gear means known per se and not expressly illustrated when the operating rod 16 is displaced in relation to the shaft 12.

The shaft 12 and the operating rod 16 are held in a handle part 18. The handle part 18 has a housing part 20, in which the shaft 12 is held, and an actuating part 22, in which the operating rod 16 is held and via which this can be actuated, in particular, by pulling and pushing. Housing part 20 and actuating part 22 of the handle part 18 are connected via a connecting shaft 24, in which the operating rod 16 is guided. The actuating part 22 has a lateral handle 26. The operating rod 16 is coupled to this handle 26 via a suitable coupling unit 28 illustrated only schematically in the drawings so that it may be displaced in a longitudinal direction via the actuation of the handle 26. The coupling unit 28 is designed accordingly such that the operating rod 16 may be released from the coupling unit 28 when the shaft 12 is released.

Figure 2:
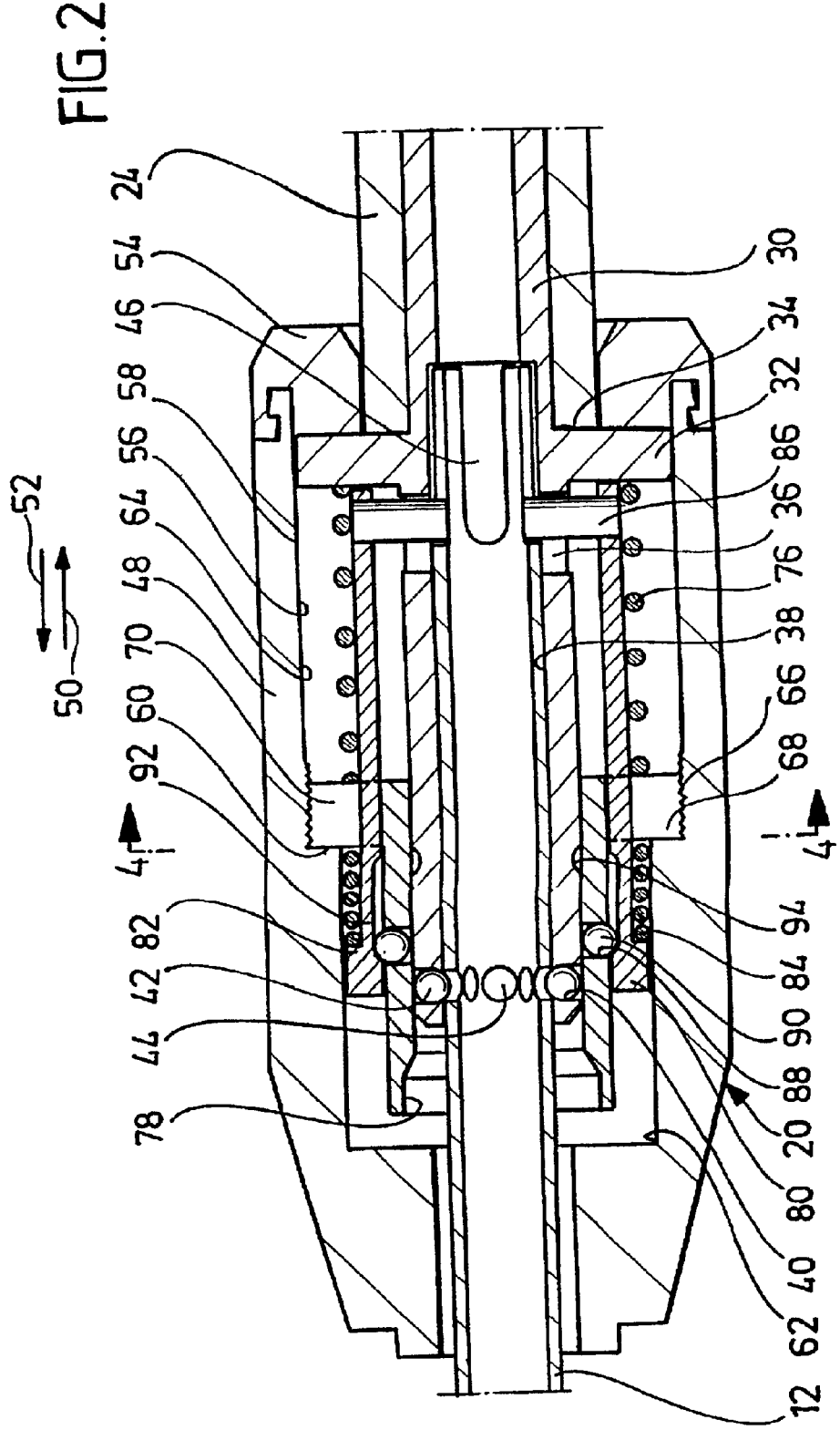
FIG. 2 shows an enlarged longitudinal sectional view of the area A in FIG. 1 with a locked shaft (connection position)

An inner sleeve 30 is arranged in the connecting shaft 24 coaxially to it and this sleeve accommodates the shaft 12 and secures it in the housing part 20. The inner sleeve 30 thereby has a plate-like element 32 which points radially outwards and abuts on a front end face 34 of the connecting shaft 24 (FIG. 2). The plate-like element 32 has a slot lying at a small angle to the radial direction, this slot serving for the insertion of a pressure spring (this slot is not shown in the drawings).

Through openings 36 are formed in the inner sleeve 30 and an interior 38 of the inner sleeve 30 can be accessed through them.

Furthermore, the inner sleeve 30 is provided with recesses 40 in the vicinity of its front end, wherein an, in particular, spherical locking member 42 is seated in such a recess 40 and is displaceable radially in it.

The shaft 12 has bowl-shaped recesses 44 which correspond to the locking members 42 and into which such a locking member 42 can dip for fixing the shaft 12 in the housing part 20. The shaft 12 has at its proximal end groove-like recesses 46 which extend in an axial direction and serve, as described later on, for the engagement of a corresponding coupling element which can engage in such a recess 46 in the shaft 12 via a recess 40 in the inner sleeve 30.

The housing part 20 has a sliding handle 48 which is longitudinally displaceable in an axial direction with respect to the connecting shaft 24. In the connection position shown in FIG. 2, in which the shaft 12 is held in the housing part 20, the sliding handle is displaceable in the proximal direction 50. In the release position shown in FIG. 3, in which the shaft 12 is released from the housing part 20, the sliding handle 48 is displaceable in the distal direction 52.

A stop nut 54 is seated at the rear end of the sliding handle 48 and this abuts in the connection position on the plate-like surface of the plate-like element 32 facing the connecting shaft 24 and thus limits the displaceability of the sliding handle 48 in the distal direction 52 (FIG. 2).

An annular interior 56 is formed between the sliding handle 48 and the inner sleeve 30 within the housing part 20. The annular interior 56 is designed in two parts by way of a step 60 in an inner boundary 58 of the sliding handle 48 and comprises a front annular chamber 62 and a rear annular chamber 64 which has a greater diameter than the front annular chamber 62 on account of the step 60. The sliding handle 48 is provided with an internal thread 66 at the step 60 towards the rear annular chamber 64. A stop element 68 designed in the shape of a sleeve is screwed into this internal thread 66 so that this is displaced along with displacement of the sliding handle 48. The stop element 68 is guided on the inner sleeve 30 surrounding it (FIG. 4). At its rear end, the stop element 68 has a nut 70 which is formed thereon in one piece and is provided with an external thread for engaging in the internal thread 66 of the sliding handle 48.

The outer diameter of this nut 70 corresponds essentially to the diameter of the rear annular chamber 64. The nut 70 has, with respect to the longitudinal direction of the housing part 20, continuous recesses 72 which are arranged, in particular, so as to be located diametrically opposite one another (FIG. 4). A limiting surface 74 of such a recess 72, which is the inner surface with respect to the inner sleeve 30, is of a circular design coaxially to the stop element 68.

A return spring 76 is seated between the proximal end face of the nut 70 and the distal end face of the plate-like element 32 in the rear annular chamber 64. For the longitudinal displacement of the sliding handle 48 out of the connection position this must be moved contrary to the restoring force of the return spring 76 which acts in the distal direction 52. The restoring force of the return spring 76 causes a longitudinal displacement of the sliding handle 48 out of the release position (FIG. 3) in the distal direction 52 into the connection position which is shown in FIG. 2.

Figure 3:
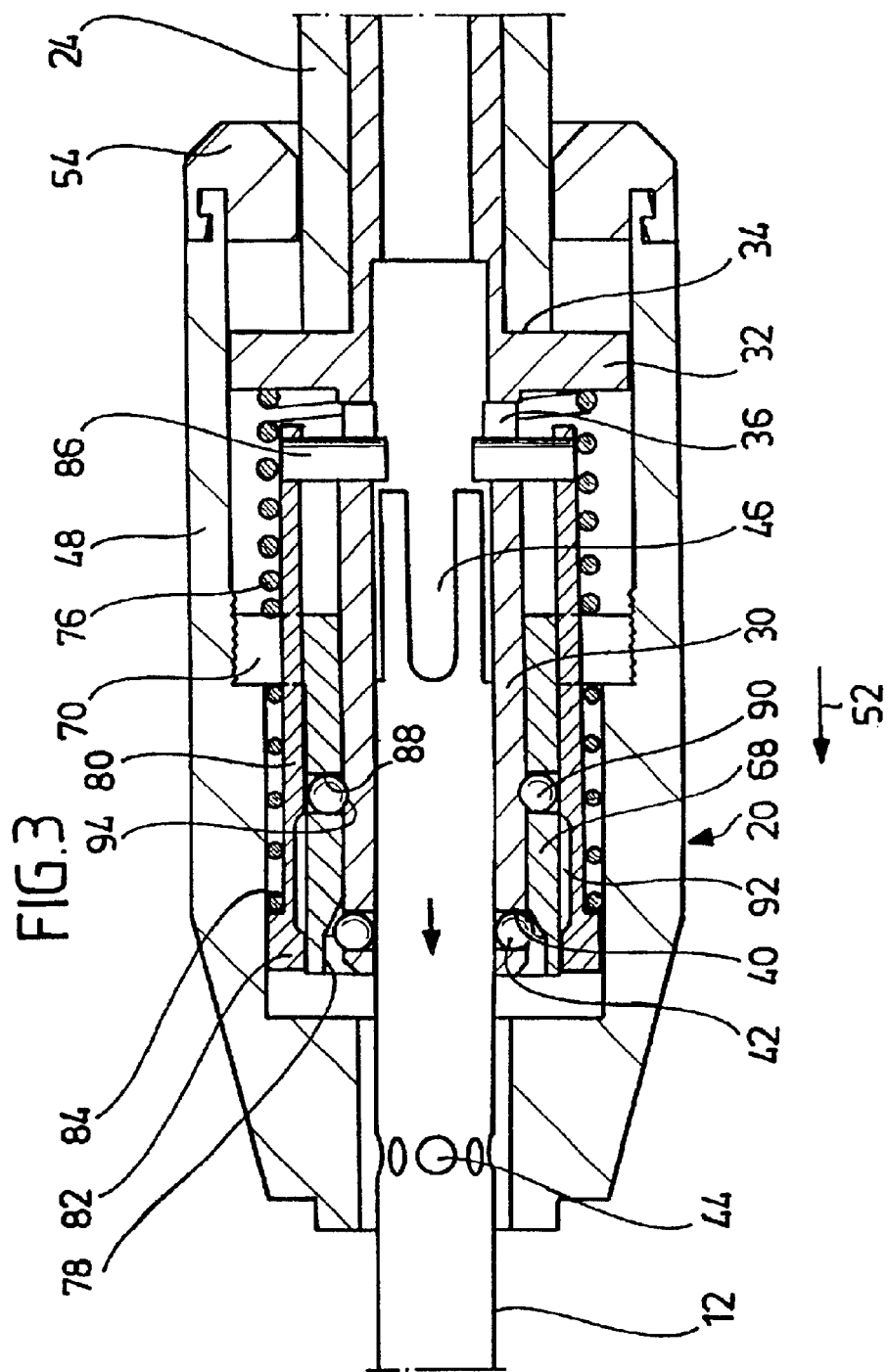

The stop element 68 has at its front end facing the inner sleeve 30 an annular recess 78 which has an area narrowing constantly in a radial direction. The stop element 68 serves, as shown in FIG. 2, to limit the radial outward movement of the locking member 42 when the stop element 68 and, with it, the sliding handle 48 are in the connection position. In this way, the shaft 12 can be secured at the housing part 20 by means of the stop element 68 due to a locking member 42 dipping into the bowl-shaped recess 44. The annular recess 78, when it is located opposite a locking member 42, as shown in FIG. 3, allows a radial outward movement of the locking member 42 in order to release the shaft 12, i.e. to discontinue the coupling with the inner sleeve 30.

A holding element 80 of a sleeve-like design is, furthermore, arranged for displacement in the interior 56. This holding element 80 is guided for displacement in the front annular chamber 62 between the sleeve-like stop element 68 and the corresponding boundary 58 of the sliding handle 48 and at the limiting surface 74 of the nut 70. It extends through the recess 72 in the nut 70 into the rear annular chamber 64. At its front (distal) end the holding element 80 has a step, the radial height of which corresponds essentially to the distance between the stop element 68 and the boundary 58 of the sliding handle 48 in the front annular chamber 62. This step serves as a stop element for a helical spring 84 which is seated between this step 82 and the nut 70. In the connection position according to FIG. 2, this helical spring 84 is tensioned, i.e. the helical spring exerts a spring force in the distal direction 52 on the holding element 80 via the step 82. The holding element 80 has coupling pins 86 which act as coupling elements, are seated on the holding element 80 so as to point radially inwards and project beyond the openings 36 in the inner sleeve 30 into its interior 38. In the connection position according to FIG. 2, the coupling pins 86 abut on the corresponding, groove-shaped recess 46 of an inserted shaft 12 and thus limit the displaceability of the holding element 80 in the distal direction 52.

Recesses 88 continuous in a radial direction are arranged in the stop element 68 and these recesses serve to accommodate locking members 90 which are, in particular, spherical. The locking members 90 are displaceable in a radial direction in these recesses 88 and have a greater diameter than the corresponding wall thickness of the stop element 68, in which the locking members 90 are seated. The holding element 80 has, facing such a locking member 90, a recess 92 in radial direction which also extends in longitudinal direction so that this is ring-shaped facing the inner sleeve 30. A locking member 90 can be guided in such a recess 92. Furthermore, the inner sleeve 30 has a bowl-shaped recess 94, into which such a locking member 90 can dip when this is displaced in a guided manner in the recess 92 in a proximal direction as far as the recess 94 with the stop element 68. The recess 92 has such a length in axial direction that, when a locking member 90 dips into the bowl-like recess 94 of the inner sleeve 30, a recess-free area of the holding element 80 can move over the locking member 90 and, as a result, acts as a stop member for its radial outward movement and prevents this (FIG. 3).

The return spring 76 is preferably designed and tensioned such that its spring force in the connection position is greater than that of the helical spring 84 for the displacement of the holding element 80.

The inventive surgical tubular-shafted instrument functions as follows:

In the connection position which is shown in FIG. 2, the shaft 12 is held in the housing part 20, i.e. is connected to the handle part 18. For this purpose, the locking members 42 dip into the corresponding recesses 44 of the shaft 12 and the stop element 68 is located over these locking members 42 such that they abut on the stop element 68, i.e. their radial outward movement is blocked. Furthermore, the coupling pins 86 of the holding element 80 are located in the recesses 46 and thus block any rotary movement of the shaft 12, in addition. The displacement of the holding element 80 is blocked in the distal direction 52 on account of the force of the helical spring 84 due to abutment of the coupling pins 86 on the distal end of the recesses 46.

In order to release the shaft 12 from the housing part 20, an operator must displace the sliding handle 48 in the proximal direction 50 contrary to the spring force of the return spring 76. As a result, the return spring 76 is pressed together and, as explained, exerts a force on the stop element 68 in the distal direction 52 via the nut 70. As a result of displacement of the sliding handle 48, the stop element 68 is displaced as well and, as a result, when the recess 78 in the front end of the stop element 68 reaches the locking members 42, such a member can move radially outwards out of the recess 44 and therefore release the shaft 12.

As a result of displacement of the stop element 68, the locking members 90 mounted therein are likewise carried along via the recess 92 in the holding element 80 until they can dip into the corresponding recesses 94 of the inner sleeve 30. As a result, the locking members 90 move radially inwards and the corresponding distances in the case of the inventive surgical tubular-shafted instrument are dimensioned such that the release position for the locking members 42 corresponds exactly to the dip-in position of the locking members 90. As a result, the shaft 12 again no longer limits the displaceability of the holding element 80 in the distal direction 52. On account of the spring force of the helical spring 84, the holding element 80 is then displaced forwards and takes the shaft 12 forwards with it due to abutment on the distal end of the recesses 46, i.e. the holding element 80 acts as an ejector for the shaft 12. Due to the forward movement of the holding element 80 in the distal direction 52, which takes place relative to the stop element 68, the holding element 80 is moved over the locking members 90 in the recesses 94 and so their radial outward movement is blocked by means of the holding element 80. As a result, the position of the stop element 68 is, however, fixed relative to the inner sleeve 30 and therefore to the housing part 20 and the sliding handle 48 is consequently fixed via the coupling to the nut 70 in a release position, in which the shaft 12 is released, i.e. is no longer held on the housing part 20 (FIG. 3). A further displacement of the holding element 80 in the distal direction 52 is blocked in that the coupling pins 86 abut on the front end of the openings 36 of the inner sleeve 30.

In order to connect a shaft 12 to the handle part 18 proceeding from this release position of the housing part 20, an operator inserts the shaft 12 in a proximal direction 50 into the inner sleeve 30 and aligns the recesses 46 with the coupling pins 86. The holding element 80 is taken along contrary to the action of the spring force of the helical spring 84 by the front end of these recesses 46 when a force is exerted in the proximal direction 50 via the coupling pins 86. As a result, the recess 92 is guided over the locking members 90 so that they can move radially outwards due to action of the spring force of the return spring 36 and are thus displaced out of the recesses 94 in the inner sleeve 30. As a result, the fixing of the stop element 68 on the inner sleeve 30 is released and the return spring 76 moves the stop element 68 in the distal direction 52. In this way, a locking member 42 is pressed radially inwards by means of the narrowing area of the recess 78 at the front end of the stop element 68 and so it can engage in an oppositely located recess 44 in the shaft 12. The stop element 68 then moves over the inner sleeve 30 in such a manner that the radial outward movement of the locking members 42 is blocked. The connection position is reached when the locking members 42 dip into the corresponding recesses 44 in the shaft 12 and the stop nut 54 has reached its stop position. The displaceability of the holding element 80 forwards (in the distal direction) is limited by the recesses 46, in which the coupling pins 86 engage, during the displacement of the stop element 68 and the holding element is moved back relative to the stop element 68 on account of the return spring 76, which exerts a greater spring force, in the direction opposite to the displacement of this stop element so that the helical spring 84 is tensioned and exerts a force in the connection position. As a result, the coupling pins 86 are also moved back with the holding element 80 relative to the openings 36. In the connection position, the coupling pins 86 engage in the recess 46 in such a manner that they secure the shaft 12 against rotation in addition to the locking members 42.

The connection or release of the operating rod 16 to or from the actuating part 22 is brought about in a known manner, for example, in such a manner that the operating rod 16 has a spherical coupling element at its end and the coupling unit 28 has a guide channel for this coupling element and the guide channel can be aligned due to corresponding positioning of the handle 26 such that the coupling element can be released from it, i.e. can be withdrawn.

What is claimed is:

1. Surgical, tubular-shafted instrument comprising a shaft, an operating rod mounted for displacement in the shaft, a handle part for actuating the operating rod and connecting means connecting the handle part and the shaft detachably to one another, wherein the shaft is securable in an axial direction in an inner sleeve of the handle part by means of a locking member displaceable radially in the inner sleeve and dipping into a recess of the shaft, the radial outward movement of said locking member being limited by a stop element displaceable into a position releasing the radial outward movement of the locking member, and wherein holding means are provided for fixing the stop element in a release position, said holding means being acted upon by the shaft in such a manner that this fixing is releasable due to displacement of the shaft in the inner sleeve, wherein the holding means comprise a holding element guided for displacement in the handle part outside the inner sleeve.

2. Instrument as defined in claim 1, wherein the holding element is guided for displacement about the inner sleeve.

3. Instrument as defined in claim 1, wherein the holding element has a coupling element for the shaft pointing into the interior of the inner sleeve.

4. Instrument as defined in claim 3, wherein the inner sleeve has a recess for the coupling element.

5. Instrument as defined in claim 3, wherein the shaft has a guiding recess for the coupling element.

6. Instrument as defined in claim 3, wherein the holding element exerts an advancing force on the shaft in a distal direction when the release position of the locking member is reached, said locking member being displaceable radially in the inner sleeve.

7. Instrument as defined in claim 3, wherein the shaft is adapted to be secured by the coupling element so as to be non-rotatable with respect to the inner sleeve.

8. Instrument as defined in claim 1, wherein the holding element is guided for displacement surrounding the stop element.

9. Instrument as defined in claim 1, wherein a spring for the relative displacement between holding element and stop element is seated between holding element and stop element and is tensioned in the connection position of the shaft.

10. Instrument as defined in claim 9, wherein the spring force acts contrary to the direction, in which the stop element is displaceable for the release of the radial outward movement of the locking member.

11. Instrument as defined in claim 9, wherein the spring seated between holding element and stop element is designed and tensioned such that it exerts a smaller spring force in the connection position than a return spring seated between stop element and inner sleeve and serving to displace the stop element out of a release position into the connection position when the fixing of the holding element is released.

12. Instrument as defined in claim 1, wherein the holding means comprise a locking member displaceable radially in the stop element and dipping into a recess of the inner sleeve in the release position of the stop element.

13. Instrument as defined in claim 12, wherein the radial outward movement of the locking member is limited in the release position of the stop element by the holding element as stop.

14. Instrument as defined in claim 12, wherein the holding element has a guiding recess for the locking member, said locking member being guided in said recess for longitudinal displacement during the displacement of the holding element from its position in the connection position into a position in the release position of the stop element.

15. Instrument as defined in claim 1, wherein the stop element is designed as a sleeve surrounding the inner sleeve.

16. Instrument as defined in claim 1, wherein the holding element is designed as a sleeve surrounding the stop element.

17. Instrument as defined in claim 1, wherein a guide means for the holding element is formed in the handle part in an annular space limited by the stop element.

18. Surgical, tubular-shafted instrument comprising a shaft, an operating rod mounted for displacement in the shaft, a handle part for actuating the operating rod and connecting means connecting the handle part and the shaft detachably to one another, wherein the shaft is securable in an axial direction in an inner sleeve of the handle part by means of a locking member displaceable radially in the inner sleeve and dipping into a recess of the shaft, the radial outward movement of said locking member being limited by a stop element displaceable into a position releasing the radial outward movement of the locking member, and wherein holding means are provided for fixing the stop element in a release position, said holding means being acted upon by the shaft in such a manner that this fixing is releasable due to displacement of the shaft in the inner sleeve, wherein the holding means have a holding element with a coupling element for securing the shaft non-rotatably with respect to the inner sleeve due to engagement in a corresponding counterelement of the shaft.

19. Instrument as defined in claim 18, wherein the counterelement is formed by a recess in the shaft.

20. Instrument as defined in claim 18, wherein the holding element is guided for displacement outside the inner sleeve.

21. Instrument as defined in claim 20, wherein the holding element is guided for displacement about the inner sleeve.

22. Instrument as defined in claim 18, wherein the holding element has a coupling element for the shaft pointing into the interior of the inner sleeve.

23. Instrument as defined in claim 22, wherein the inner sleeve has a recess for the coupling element.

24. Instrument as defined in claim 18, wherein the holding element exerts an advancing force on the shaft in a distal direction when the release position of the locking member is reached, said locking member being displaceable radially in the inner sleeve.

25. Instrument as defined in claim 18, wherein the holding element is guided for displacement surrounding the stop element.

26. Instrument as defined in claim 18, wherein a spring for the relative displacement between holding element and stop element is seated between holding element and stop element and is tensioned in the connection position of the shaft.

27. Instrument as defined in claim 26, wherein the spring force acts contrary to the direction, in which the stop element is displaceable for the release of the radial outward movement of the locking member.

28. Instrument as defined in claim 26, wherein the spring constant of the spring seated between holding element and stop element is designed and tensioned such that it exerts a smaller spring force in the connection position than a return spring seated between stop element and inner sleeve and serving to displace the stop element out of a release position into the connection position when the fixing of the holding element is released.

29. Instrument as defined in claim 18, wherein the holding means comprise a locking member displaceable radially in the stop element and dipping into a recess of the inner sleeve in the release position of the stop element.

30. Instrument as defined in claim 29, wherein the radial outward movement of the locking member is limited in the release position of the stop element by the holding element as stop.

31. Instrument as defined in claim 29, wherein the holding element has a guiding recess for the locking member, said locking member being guided in said recess for longitudinal displacement during the displacement of the holding element from its position in the connection position into a position in the release position of the stop element.

32. Instrument as defined in claim 18, wherein the stop element is designed as a sleeve surrounding the inner sleeve.

33. Instrument as defined in claim 18, wherein the holding element is designed as a sleeve surrounding the stop element.

34. Instrument as defined in claim 18, wherein a guide means for the holding element is formed in the handle part in an annular space limited by the stop element.

* * * * *